United States Patent
Lee et al.

(10) Patent No.: US 11,883,634 B2
(45) Date of Patent: Jan. 30, 2024

(54) ELECTROHYDRAULIC MICROJET DRUG DELIVERY DEVICE

(71) Applicant: MEDIJET CO., LTD., Jinju-si (KR)

(72) Inventors: Seok Soon Lee, Jinju-si (KR); Jin Kyu Choi, Gimhae-si (KR); Han Bin Kang, Jinju-si (KR); Seung Min Tak, Jinju-si (KR); In Seok Baek, Geoje-si (KR)

(73) Assignee: MEDIJET CO., LTD., Jinju-si (KR)

( * ) Notice: Subject to any disclaimer, the term of this patent is extended or adjusted under 35 U.S.C. 154(b) by 370 days.

(21) Appl. No.: 17/045,676

(22) PCT Filed: Apr. 4, 2019

(86) PCT No.: PCT/KR2019/003974
§ 371 (c)(1),
(2) Date: Oct. 6, 2020

(87) PCT Pub. No.: WO2019/198971
PCT Pub. Date: Oct. 17, 2019

(65) Prior Publication Data
US 2021/0023304 A1    Jan. 28, 2021

(30) Foreign Application Priority Data
Apr. 9, 2018 (KR) .......... 10-2018-0040865

(51) Int. Cl.
*A61M 5/30* (2006.01)
*A61M 5/31* (2006.01)

(52) U.S. Cl.
CPC .......... *A61M 5/30* (2013.01); *A61M 5/31* (2013.01); *A61M 2005/3128* (2013.01); *A61M 2205/8262* (2013.01)

(58) Field of Classification Search
CPC ........ A61M 5/30; A61M 5/31; A61M 5/2046; A61M 2005/3128; A61M 2205/8262; A61M 2039/242; A61M 11/02
See application file for complete search history.

(56) References Cited

U.S. PATENT DOCUMENTS 8,905,966 B2 * 12/2014 Yoh .......... A61M 5/30
604/141
11,400,219 B2 * 8/2022 Yoh .......... A61M 5/3007
(Continued)

FOREIGN PATENT DOCUMENTS

CN  1777452 A  *  5/2006  .......... A61M 15/025
CN  1777452 A     5/2006
(Continued)

*Primary Examiner* — Brandy S Lee
*Assistant Examiner* — Fatimata Sahra Diop
(74) *Attorney, Agent, or Firm* — NKL LAW; Jae Youn Kim

(57) ABSTRACT

An electrohydraulic microjet drug delivery device includes: a discharge body provided with a power supply unit in which electric energy is stored; and a medicinal fluid delivery body detachably attached to the discharge body, the medicinal fluid delivery body including a pressure generation unit configured to store a pressure generation liquid, a medicinal fluid storage unit configured to store a medicinal fluid, an elastic separation membrane installed between the pressure generation unit and the medicinal fluid storage unit and configured to separate the pressure generation liquid and the medicinal fluid, a discharger installed inside the pressure generation unit so as to be submerged in the pressure generation liquid and configured to generate a spark using the electric energy stored in the power supply unit, and a nozzle kept in communication with the medicinal fluid storage unit.

5 Claims, 4 Drawing Sheets

(56) References Cited

U.S. PATENT DOCUMENTS

| | | | | |
|---|---|---|---|---|
| 2001/0027293 A1* | 10/2001 | Joshi | ............... | A61M 5/30 |
| | | | | 604/131 |
| 2013/0066263 A1* | 3/2013 | Yoh | ............... | A61M 5/30 |
| | | | | 604/70 |
| 2015/0265770 A1* | 9/2015 | Yoh | ............... | A61M 5/30 |
| | | | | 604/70 |
| 2018/0036486 A1* | 2/2018 | Yamamoto | ............ | A61M 5/315 |
| 2018/0154082 A1* | 6/2018 | Yoh | ............... | A61M 5/2046 |

FOREIGN PATENT DOCUMENTS

| | | | |
|---|---|---|---|
| JP | 5-184674 A | 7/1993 | |
| JP | 2016-198328 A | 12/2016 | |
| JP | 2017-154173 A | 9/2017 | |
| KR | 10-2005-0055723 A | 6/2005 | |
| KR | 10-0539885 B1 | 12/2005 | |
| KR | 20110027305 A * | 3/2011 | |
| KR | 20110027305 A * | 3/2011 | |
| KR | 10-1207977 B1 | 12/2012 | |
| KR | 10-2014-0021383 A | 2/2014 | |
| KR | 2014-0140739 A | 12/2014 | |
| KR | 10-1549966 B1 | 9/2015 | |
| KR | 2015-0100105 A | 9/2015 | |
| KR | 10-1684250 B1 | 12/2016 | |
| KR | 10-1834773 B1 | 3/2018 | |
| KR | 101834773 B1 * | 3/2018 | |
| KR | 101834773 B1 * | 3/2018 | ............ A61M 37/00 |

\* cited by examiner

ELECTROHYDRAULIC MICROJET DRUG DELIVERY DEVICE

TECHNICAL FIELD

The present invention relates to a microjet drug delivery device, and more particularly, to an electrohydraulic microjet drug delivery device that deforms an elastic separation membrane to inject a drug by discharging high-density energy to a liquid separated from the drug by the elastic separation membrane and rapidly vaporizing the liquid.

BACKGROUND ART

As a drug delivery system for injecting a drug into a body, a syringe having a needle has been traditionally used. However, such a traditional syringe has been the subject of fear to patients due to the pain during injection, and has an inevitable problem such as a likelihood of infection due to a wound or the like.

In order to solve this problem, drug delivery systems such as a needle-free injector and the like are being developed. As a part of this research, there has been proposed a drug delivery system in which a drug is injected at high speed in a microjet method so as to directly penetrate into a body through the epidermis of a skin.

In order to cause such a high-speed injection using the microjet method, it is necessary to precisely and powerfully inject the drug to the outside (i.e., the skin). This injection method has been developed in various ways since the 1930s. Recently, there have been developed various injection methods such as an injection method using a piezoelectric ceramic element, an injection method using shock waves generated by applying a laser beam to an aluminum foil, an injection method using a Lorentz force, and the like. Furthermore, in recent years, there has been developed a reusable laser-bubble-type microjet injection method capable of, unlike the conventional microjet injection methods, finely adjusting an amount of a drug to be injected and an injection speed of a drug while performing continuous injection. However, there are limitations in miniaturization and dissemination due to the size and cost of laser equipment.

PRIOR ART DOCUMENT

Patent Document

Patent Document 1: Korean Patent Application Publication No. 10-2005-7004979
Patent Document 2: Korean Patent Application Publication No. 10-2010-0056637
Patent Document 3: Korean Patent Application Publication No. 10-2012-0087843
Patent Document 4: Korean Patent Application Publication No. 10-2014-0021473
Patent Document 5: Korean Patent Application Publication No. 10-2017-0111150

SUMMARY

With the aforementioned problems in view, it is an object of the present invention to provide an electrohydraulic microjet drug delivery device that deforms an elastic separation membrane to inject a drug by discharging high-density energy to a liquid separated from the drug by the elastic separation membrane and rapidly vaporizing the liquid.

Another object of the present invention is to provide an electrohydraulic microjet drug delivery device capable of being manufactured at low cost due to its simple structure and capable of easily controlling a pressure or a speed of microjet as desired.

A further object of the present invention is to provide an electrohydraulic microjet drug delivery device capable of enabling a user to easily replace a cartridge-type drug container, thereby solving a hygiene problem, protecting an environment, and saving resources.

According to one aspect of the present invention, there is provided an electrohydraulic microjet drug delivery device, including: a discharge body provided with a power supply unit in which electric energy is stored; and a medicinal fluid delivery body detachably attached to the discharge body, the medicinal fluid delivery body including a pressure generation unit configured to store a pressure generation liquid, a medicinal fluid storage unit configured to store a medicinal fluid, an elastic separation membrane installed between the pressure generation unit and the medicinal fluid storage unit and configured to separate the pressure generation liquid and the medicinal fluid, a discharger installed inside the pressure generation unit so as to be submerged in the pressure generation liquid and configured to generate a spark using the electric energy stored in the power supply unit, and a nozzle kept in communication with the medicinal fluid storage unit, wherein when the spark is generated in the discharger, a part of the pressure generation liquid is vaporized and expanded to deform the elastic separation membrane toward the medicinal fluid storage unit so that the medicinal fluid is injected through the nozzle.

The device may further include: a first terminal installed on the discharge body and connected to the power supply unit; and a second terminal installed on the medicinal fluid delivery body and connected to the discharger, wherein when the discharge body and the medicinal fluid delivery body are coupled, the first terminal and the second terminal may come into contact with each other so that the electric energy stored in the power supply unit is transferred to the discharger.

In the device, plasma of high temperature and high pressure may be generated locally in the pressure generation unit by the spark generated in the discharger.

In the device, the discharge body may include a power supply unit in which electric energy is stored, a coupling unit in which the medicinal fluid delivery body is detachably accommodated, and a first terminal provided inside the coupling unit, and an electric wire configured to connect the power supply unit and the first terminal.

The device may further include: a check valve installed between the nozzle and the medicinal fluid storage unit.

In the device, the medicinal fluid storage unit may be detachably attached to the pressure generation unit.

The electrohydraulic microjet drug delivery device according to the present invention can deform the elastic separation membrane to inject the drug by discharging high-density energy to the liquid separated from the drug by the elastic separation membrane and rapidly vaporizing the liquid. In this manner, the drug can be caused to rapidly penetrate into the tissue through the skin.

Furthermore, the electrohydraulic microjet drug delivery device according to the present disclosure can be manufactured at low cost due to its simple structure and can easily control a pressure or a speed of microjet.

In addition, the electrohydraulic microjet drug delivery device according to the present invention can enable a user to easily replace a cartridge-type drug container, thereby solving a hygiene problem, protecting an environment, and saving resources.

DETAILED DESCRIPTION

Figure 1:
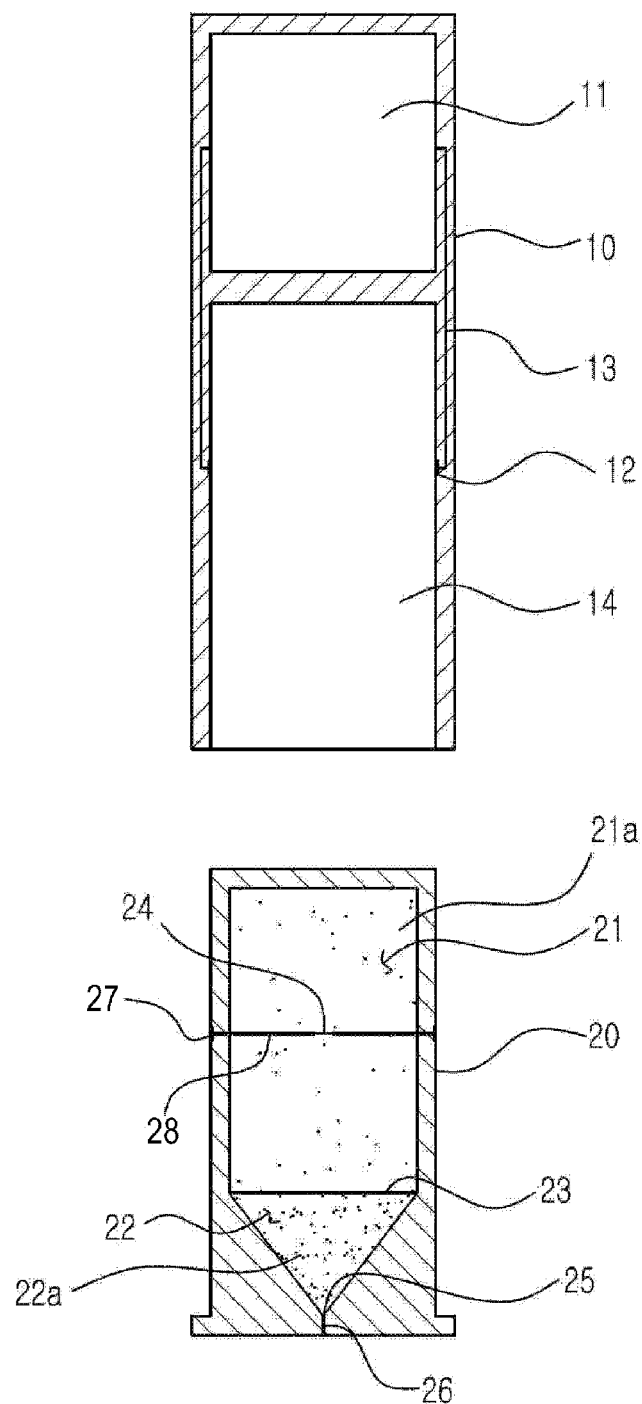
FIG. 1 is an exploded view showing an electrohydraulic microjet drug delivery device according to one embodiment of the present invention.

Hereinafter, preferred embodiments of the present invention will be described in detail with reference to the accompanying drawings. The embodiments of the present invention may be modified in various forms. The scope of the present invention should not be construed as being limited to the embodiments described below. These embodiments are provided to specifically explain the present invention to those skilled in the art. Thus, the shape of each element shown in the drawings may be exaggerated to emphasize a clearer description.

The terms "first", "second" and the like may be used to describe various elements. However, the elements should not be limited by these terms. The terms are used only for the purpose of distinguishing one component from another.

The terms referred to herein are used merely for the purpose of describing particular embodiments and are not intended to limit the present invention. A singular form includes a plural form unless the context clearly dictates otherwise. In this application, the terms "include", "have" and the like are used to specify the existence of a feature, a figure, a step, an operation, an element, a part or a combination thereof described in the specification and are not intended to exclude the existence or the possibility of addition of one or more other features, figures, steps, operations, components, parts, or combinations thereof.

As shown in FIG. 1, the electrohydraulic microjet drug delivery device according to one embodiment of the present invention includes a discharge body 10 and a medicinal fluid delivery body 20.

The discharge body 10 includes a power supply unit 11 in which a certain amount of electric energy is stored, a coupling unit 14 having a space separated from the power supply unit 11, a first terminal 12 provided inside the coupling unit 14, and an electric wire 13 configured to electrically connect the first terminal 12 and the power supply unit 11. The power supply unit 11 may include, for example, one or more capacitors.

In this regard, the power supply unit 11 may be charged through an external power source.

The medicinal fluid delivery body 20 includes a pressure generation unit 21 configured to store pressure generation liquid 21a, a medicinal fluid storage unit 22 configured to store a medicinal fluid 22a, an elastic separation membrane 23 configured to separate the pressure generation unit 21 and the medicinal fluid storage unit 22, a second terminal 27 provided outside the medicinal fluid delivery body so as to make contact with the first terminal 12, electrodes 28 disposed inside the pressure generation unit 21 and connected to the second terminal 27, a discharger 24 configured to connect the electrodes 28, and a nozzle 26 kept in communication with the medicinal fluid storage unit 22 and configured to inject the medicinal fluid stored in the medicinal fluid storage unit 22 to the outside.

A check valve 25 may be installed between the medicinal fluid storage unit 22 and the nozzle 26 to prevent the medicinal fluid from flowing out of the medicinal fluid storage unit 22 until a pressure is generated.

Hereinafter, the operation of the electrohydraulic microjet drug delivery device according to one embodiment of present invention will be described with reference to FIGS. 2 and 3.

Figure 2:
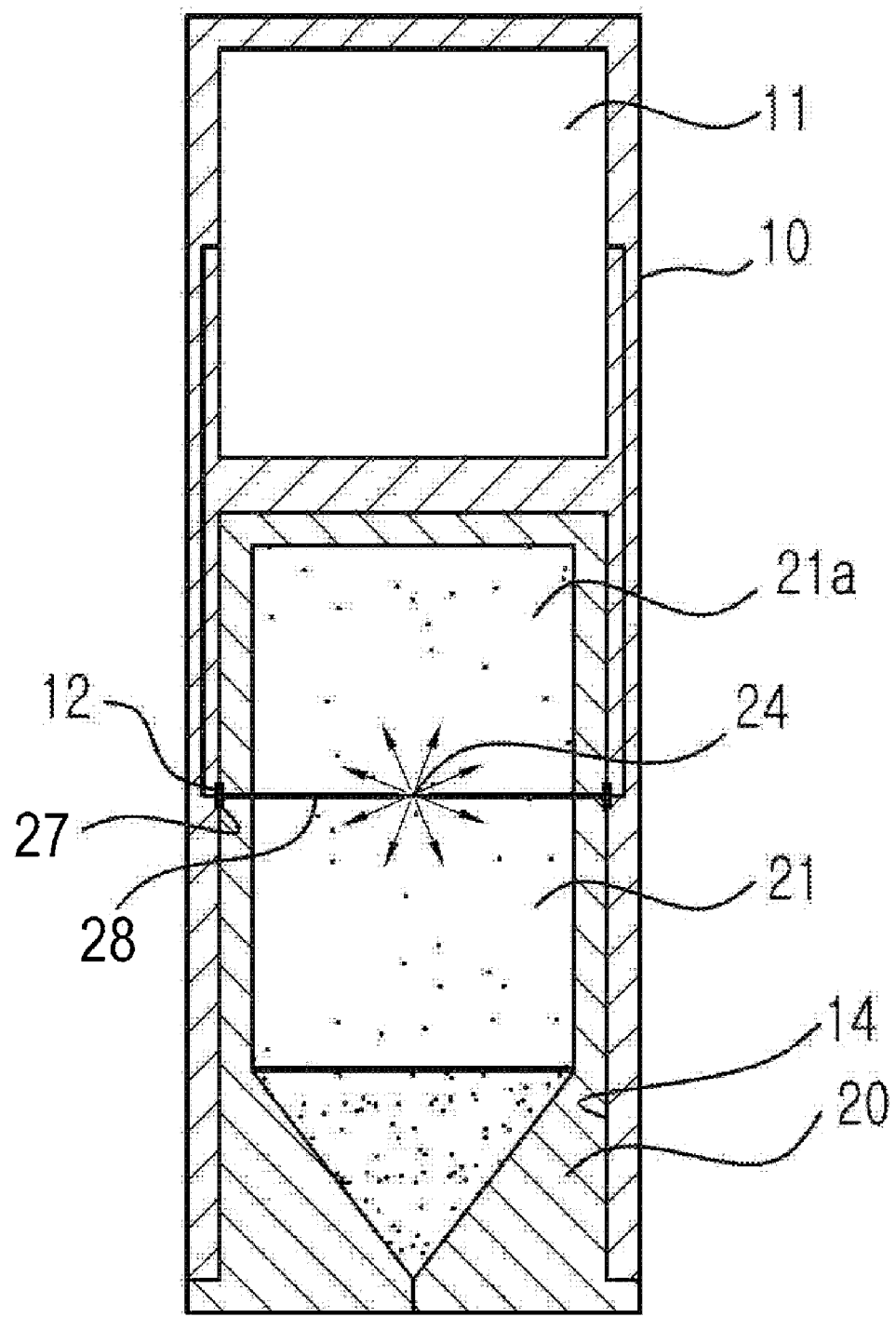
FIGS. 2 and 3 are operation diagrams showing the operation of the electrohydraulic microjet drug delivery device according to one embodiment of the present invention.

First, as shown in FIG. 2, the medicinal fluid delivery body 20 is inserted into the coupling unit 14 of the discharge body 10.

Upon insertion, the second terminal 27 of the medicinal fluid delivery body 20 makes contact with the first terminal 12 of the discharge body 10, whereby the electric energy stored in the power supply unit 11 is supplied to the electrode 28.

A spark is generated by the supplied electric energy in the discharger 24 that connects the electrodes 28. Thus, a part of the pressure generation liquid 21a stored in the pressure generation unit 21 is instantaneously vaporized and rapidly expanded in volume. The gas may come into a plasma state of high temperature and high pressure.

Figure 3:
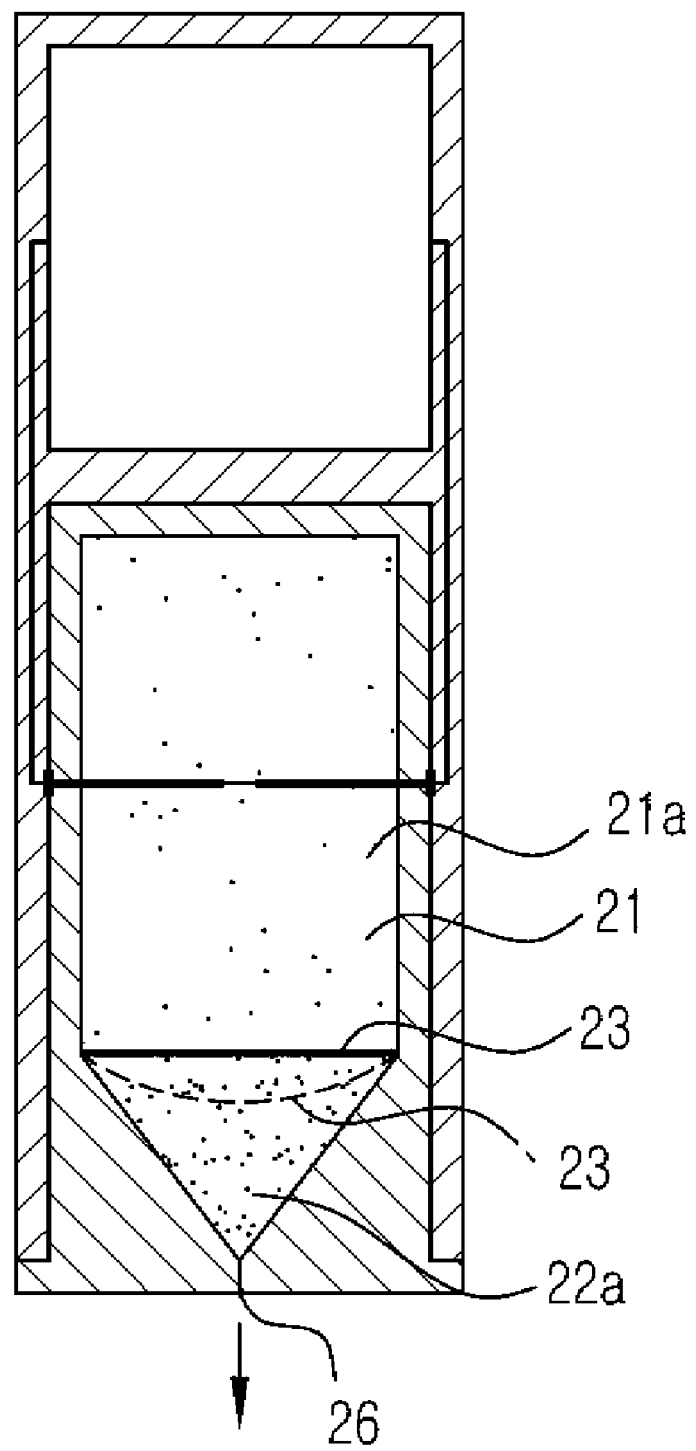

Due to the pressure generated at this time, as shown in FIG. 3, the elastic separation membrane 23 disposed to separate the pressure generation unit 21 and the medicinal fluid storage unit 22 is rapidly expanded toward the medicinal fluid storage unit 22 to increase the pressure in the medicinal fluid storage unit 22, whereby the medicinal fluid 22a in the medicinal fluid storage unit 22 is rapidly injected through the nozzle 26.

At this time, the medicinal fluid delivery body 20 is in contact with the skin on the side of the nozzle 26. Therefore, the injected medicinal fluid penetrates into the body through the skin. The used medicinal fluid delivery body 20 is separated from the discharge body 10 and disposed separately, and the discharge body 10 may be reused by charging electric energy to the power supply unit 11.

On the other hand, a check valve 25 may be separately installed between the medicinal fluid storage unit 22 and the nozzle 26. Although the medicinal fluid does not flow through the nozzle due to the viscosity of the medicinal fluid even without the use of the check valve 25, the check valve 25 can prevent foreign substances from penetrating into the medicinal fluid storage unit 22 through the nozzle, which makes it possible to store the medicinal fluid in a more hygienic manner.

In addition, when the check valve 25 is not used, it is possible to block the nozzle by using a separate film or sheet on the nozzle side lower portion of the medicinal fluid delivery body.

Figure 4:
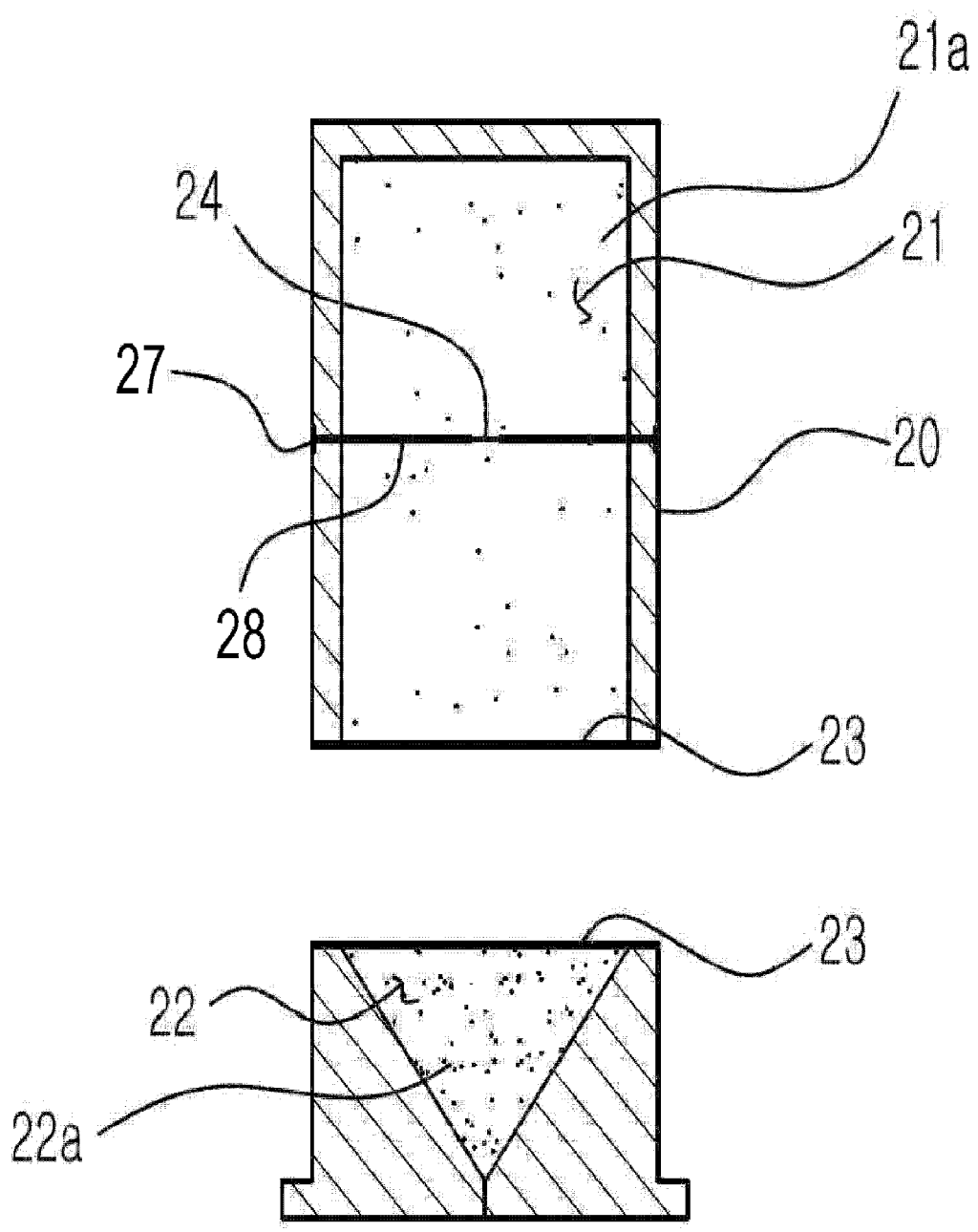
FIG. 4 is a view showing an electrohydraulic microjet drug delivery device according to another embodiment of the present invention.

FIG. 4 is a view showing an electrohydraulic microjet drug delivery device according to another embodiment of the present invention. In the embodiment shown in FIG. 4, the medicinal fluid delivery body 20 is configured so that the pressure generation unit 21 for storing the pressure generation liquid 21 and the medicinal fluid storage unit 22 for storing the medicinal fluid are detachably attached to each other. Therefore, only the medicinal fluid can be separately stored and managed. This makes it possible to manage the medicinal fluid in a more hygienic manner.

The pressure generation unit 21 and the medicinal fluid storage unit 22 may have, for example, a structure in which a protrusion and a groove are formed in a contact portion so that the upper and lower separated portions are rotated and coupled in opposite directions about an imaginary vertical axis.

In this way, the medicinal fluid can be vaporized through the use of the spark generated by the electric energy stored in the portable discharge body and can be caused to penetrate the skin. Therefore, the electrohydraulic microjet drug delivery device can be used conveniently like a general syringe, and has advantages in various aspects such as the size, the durability of use, the convenience in the storage of medicinal fluid, the environmental friendliness, and the like.

While the present invention has been described with reference to the preferred embodiment, this description is intended to enhance the understanding of the technical contents of the present invention and is not intended to limit the technical scope of the present invention.

It will be apparent to those skilled in the art that various modifications and variations can be made without departing from the spirit and scope of the invention. Needless to say, such modifications and variations fall within the technical scope of the present invention as defined by the appended claims.

What is claimed is:

1. An electrohydraulic microjet drug delivery device, comprising:
   a discharge body provided with a power supply unit in which electric energy is stored; and
   a medicinal fluid delivery body detachably attached to the discharge body, the medicinal fluid delivery body including a pressure generation unit configured to store a pressure generation liquid, a medicinal fluid storage unit configured to store a medicinal fluid, an elastic separation membrane installed between the pressure generation unit and the medicinal fluid storage unit and configured to separate the pressure generation liquid and the medicinal fluid, a pair of electrodes installed inside the pressure generation unit so as to be submerged in the pressure generation liquid and configured to be connected to the power supply unit, a discharger provided between the pair of electrodes and installed inside the pressure generation unit so as to be submerged in the pressure generation liquid and configured to generate a spark using the electric energy stored in the power supply unit, wherein a thickness of the discharger is thinner than a thickness of each of the pair of electrodes, and a nozzle kept in communication with the medicinal fluid storage unit, and
   wherein when the spark is generated in the discharger, a part of the pressure generation liquid is vaporized and expanded to deform the elastic separation membrane toward the medicinal fluid storage unit so that the medicinal fluid is injected through the nozzle, and
   wherein the discharge body includes the power supply unit in which the electric energy is stored, a coupling unit in which the medicinal fluid delivery body is detachably accommodated, and a first terminal provided inside the coupling unit, and an electric wire configured to connect the power supply unit and the first terminal.

2. The device according to claim 1, wherein a plasma is generated locally in the pressure generation unit by the spark generated in the discharger.

3. The device according to claim 1, further comprising:
   a check valve installed between the nozzle and the medicinal fluid storage unit.

4. The device according to claim 1, wherein the medicinal fluid storage unit is detachably attached to the pressure generation unit.

5. An electrohydraulic microjet drug delivery device, comprising:
   a discharge body provided with a power supply unit in which electric energy is stored;
   a medicinal fluid delivery body detachably attached to the discharge body, the medicinal fluid delivery body including a pressure generation unit configured to store a pressure generation liquid, a medicinal fluid storage unit configured to store a medicinal fluid, an elastic separation membrane installed between the pressure generation unit and the medicinal fluid storage unit and configured to separate the pressure generation liquid and the medicinal fluid, a pair of electrodes installed inside the pressure generation unit so as to be submerged in the pressure generation liquid and configured to be connected to the power supply unit, a discharger provided between the pair of electrodes and installed inside the pressure generation unit so as to be submerged in the pressure generation liquid and configured to generate a spark using the electric energy stored in the power supply unit, wherein a thickness of the discharger is thinner than a thickness of each of the pair of electrodes, and a nozzle kept in communication with the medicinal fluid storage unit;
   a first terminal installed on the discharge body and connected to the power supply unit; and
   a second terminal installed on the medicinal fluid delivery body and connected to the discharger,
   wherein when the spark is generated in the discharger, a part of the pressure generation liquid is vaporized and expanded to deform the elastic separation membrane toward the medicinal fluid storage unit so that the medicinal fluid is injected through the nozzle, and
   wherein when the discharge body and the medicinal fluid delivery body are coupled, the first terminal and the second terminal come into contact with each other so that the electric energy stored in the power supply unit is transferred to the discharger.

* * * * *